US008129327B2

(12) United States Patent
Zhang et al.

(10) Patent No.: US 8,129,327 B2
(45) Date of Patent: Mar. 6, 2012

(54) PACKAGING FOR HIGH MOISTURE BAR SOAP

(75) Inventors: Grace (Jing) Zhang, Beijing (CN); Ji-Quan Liu, Kobe (JP); Charlie Reyes Salvador, Beijing (CN)

(73) Assignee: The Procter & Gamble Company, Cincinnati, OH (US)

( * ) Notice: Subject to any disclaimer, the term of this patent is extended or adjusted under 35 U.S.C. 154(b) by 837 days.

(21) Appl. No.: 11/998,797

(22) Filed: Nov. 30, 2007

(65) Prior Publication Data

US 2009/0143267 A1 Jun. 4, 2009

Related U.S. Application Data

(60) Provisional application No. 60/872,377, filed on Dec. 1, 2006.

(51) Int. Cl.
*A61K 7/50* (2006.01)

(52) U.S. Cl. ......... 510/440; 510/141; 510/382; 510/446

(58) Field of Classification Search ........................ None
See application file for complete search history.

(56) References Cited

U.S. PATENT DOCUMENTS

| | | | |
|---|---|---|---|
| 1,475,663 | A | 11/1923 | Tseng |
| 2,267,310 | A | 12/1941 | Shearer |
| 2,438,169 | A | 3/1948 | Hoyt |
| 2,528,378 | A | 10/1950 | Mannheimer |
| 2,658,072 | A | 11/1953 | Kosmin |
| 2,982,735 | A | 5/1961 | Blinka et al. |
| 3,179,596 | A | 4/1965 | Farrar et al. |
| 3,224,976 | A | 12/1965 | Farrar et al. |
| 3,226,329 | A | 12/1965 | MacMillan |
| 3,247,121 | A | 4/1966 | Hendricks |
| 3,493,464 | A | 2/1970 | Bowers et al. |
| 3,494,869 | A | 2/1970 | Armstrong |
| 3,650,082 | A | 3/1972 | Meek |
| 3,824,189 | A | 7/1974 | Borrello |
| 3,835,058 | A | 9/1974 | White |
| 4,097,407 | A | 6/1978 | Ady |
| 4,297,230 | A | 10/1981 | Rasser |
| 4,396,521 | A | 8/1983 | Borrello |
| 4,673,525 | A | 6/1987 | Small et al. |
| 4,808,322 | A | 2/1989 | McLaughlin |
| 4,812,253 | A | 3/1989 | Small et al. |
| 4,820,447 | A | 4/1989 | Medcalf et al. |
| 4,851,147 | A | 7/1989 | Esposito et al. |
| 4,858,757 | A | 8/1989 | Liggett |
| 4,874,538 | A | 10/1989 | Dawson et al. |
| 4,877,674 | A | 10/1989 | Kappes |
| 4,946,618 | A | 8/1990 | Knochel et al. |
| 4,963,284 | A | 10/1990 | Novakovic et al. |
| 4,985,170 | A | 1/1991 | Dawson et al. |
| 5,002,685 | A | 3/1991 | Chambers et al. |
| 5,057,311 | A | 10/1991 | Kamegai et al. |
| 5,057,359 | A | 10/1991 | Merdem et al. |
| 5,064,555 | A | 11/1991 | Medcalf et al. |
| 5,076,953 | A | 12/1991 | Jordan et al. |
| 5,096,608 | A | 3/1992 | Small et al. |
| 5,098,012 | A | 3/1992 | Will |
| 5,202,048 | A | 4/1993 | Bartolo et al. |
| 5,264,144 | A | 11/1993 | Moroney et al. |
| 5,340,492 | A | 8/1994 | Kacher et al. |
| 5,387,362 | A | 2/1995 | Tollens et al. |
| 5,425,892 | A | 6/1995 | Taneri et al. |
| 5,505,370 | A | 4/1996 | Brown et al. |
| 5,631,215 | A | 5/1997 | Kinsman |
| 5,683,973 | A | 11/1997 | Post et al. |
| 5,703,026 | A | 12/1997 | Setser et al. |
| 5,705,092 | A | 1/1998 | Wellinghoff et al. |
| 5,715,657 | A | 2/1998 | Mondani et al. |
| 5,723,420 | A | 3/1998 | Wei et al. |
| 5,887,410 | A | 3/1999 | Lowenthal |
| 5,965,501 | A | 10/1999 | Rattinger et al. |
| 5,980,826 | A | 11/1999 | Barenberg et al. |
| 5,992,630 | A | 11/1999 | Brown et al. |
| 6,045,882 | A | 4/2000 | Sandford |
| 6,057,275 | A | 5/2000 | Fair et al. |
| 6,107,262 | A | 8/2000 | Noble, II |
| 6,242,397 | B1 | 6/2001 | Milio et al. |
| 6,310,016 | B1 | 10/2001 | Behal et al. |
| 6,336,553 | B1 | 1/2002 | Van Gordon |
| 6,440,908 | B2 | 8/2002 | Racherla |
| 6,488,943 | B1 | 12/2002 | Beerse et al. |
| 6,520,322 | B2 | 2/2003 | Moss |
| 6,533,165 | B2 | 3/2003 | Giblin et al. |
| 6,562,772 | B1 | 5/2003 | Maurin et al. |
| D483,150 | S | 12/2003 | Cummings |

(Continued)

FOREIGN PATENT DOCUMENTS

| | | |
|---|---|---|
| BR | 9100166 | 9/1992 |

(Continued)

OTHER PUBLICATIONS

International Search Report, PCT/IB2007/054854, dated Apr. 3, 2008 (5 pages).

(Continued)

*Primary Examiner* — Necholus Ogden, Jr.

(57) ABSTRACT

Packaging is provided for high moisture bar soap compositions to address a number of potential problems associated with high moisture bar soap compositions, such as minimizing moisture loss, inhibiting mold growth on paperboard material used in the packaging, and preventing the development of colored stains on the bar soap and packaging resulting from chemical reaction between the high moisture bar soap and the paperboard, especially recycled paperboard. The bar soap packaging comprises a laminate material comprising a paperboard material, a thermoplastic material disposed on at least one side of the paperboard material, and a fungicide. Further provided is a method of inhibiting the growth of mold on a paperboard package which can result from storage of a high moisture bar soap composition in the paperboard package by treating the paperboard package with a fungicide comprising chlorothalonil and p-tolyl diiodomethyl sulfone, and then packaging the high moisture bar soap composition in the treated paperboard package.

14 Claims, No Drawings

U.S. PATENT DOCUMENTS

| | | | |
|---|---|---|---|
| 6,841,524 | B1 | 1/2005 | Patel et al. |
| 6,849,585 | B1 | 2/2005 | Farrell et al. |
| 6,852,681 | B1 | 2/2005 | Kerschner et al. |
| 6,949,493 | B1 | 9/2005 | Zhang et al. |
| 7,045,491 | B2 | 5/2006 | Hourigan |
| 7,401,697 | B2 | 7/2008 | Moss |
| 2001/0046950 | A1 | 11/2001 | Agrawal et al. |
| 2002/0016271 | A1 | 2/2002 | Racherla |
| 2002/0166778 | A1 | 11/2002 | Moss |
| 2003/0006605 | A1 | 1/2003 | Ross |
| 2003/0087778 | A1 | 5/2003 | Moss |
| 2004/0055904 | A1 | 3/2004 | Cummings |
| 2004/0238608 | A1 | 12/2004 | Van Gordon |
| 2004/0248750 | A1 | 12/2004 | Nimmey et al. |
| 2004/0248751 | A1 | 12/2004 | Johnson et al. |
| 2005/0003975 | A1 | 1/2005 | Browne et al. |
| 2005/0035008 | A1 | 2/2005 | Nimmey et al. |
| 2005/0069861 | A1 | 3/2005 | Zimmermann et al. |
| 2005/0107273 | A1 | 5/2005 | Hourigan |
| 2005/0192192 | A1 | 9/2005 | Bouzas et al. |
| 2005/0227886 | A1 | 10/2005 | Patel et al. |
| 2006/0008513 | A1 | 1/2006 | Holbert et al. |
| 2006/0071057 | A1 | 4/2006 | Aschenbrenner et al. |
| 2006/0088495 | A1 | 4/2006 | Harichian |
| 2006/0201115 | A1 | 9/2006 | Van Gordon et al. |
| 2006/0287206 | A1 | 12/2006 | Nadakatti et al. |
| 2007/0021314 | A1 | 1/2007 | Salvador et al. |
| 2007/0155639 | A1 | 7/2007 | Salvador et al. |
| 2008/0020959 | A1 | 1/2008 | Salvador et al. |

FOREIGN PATENT DOCUMENTS

| | | | | |
|---|---|---|---|---|
| BR | 20000001057 | | | 11/2001 |
| BR | 20000001058 | | | 11/2001 |
| CA | 1117491 | | | 2/1982 |
| EP | 0209362 | A2 | | 1/1987 |
| EP | 0251410 | A1 | | 1/1988 |
| EP | 0155915 | B1 | | 11/1989 |
| EP | 0507559 | B1 | | 10/1992 |
| EP | 0249474 | B1 | | 6/1993 |
| EP | 0665915 | B1 | | 8/1995 |
| EP | 0648689 | B1 | | 4/1997 |
| FR | 895204 | | | 1/1945 |
| GB | 1365986 | | | 9/1974 |
| GB | 1430388 | | | 3/1976 |
| GB | 1585966 | | | 3/1981 |
| GB | 2271120 | A | | 4/1994 |
| GB | 2336160 | | | 10/1999 |
| IN | 2003000310 | | | 2/2005 |
| JP | 05-177792 | | | 7/1993 |
| JP | 11-105188 | | | 4/1999 |
| JP | 11-236037 | | | 8/1999 |
| JP | 2001-047546 | | | 2/2001 |
| JP | 2001-225424 | | | 8/2001 |
| JP | 2001-328623 | | | 11/2001 |
| JP | 2003-205573 | | | 7/2003 |
| JP | 2004-018027 | | | 1/2004 |
| JP | 2006-181768 | | | 7/2006 |
| KR | 2001-008338 | | | 2/2001 |
| KR | 20040072158 | A | | 8/2004 |
| WO | WO-92/05241 | A1 | | 4/1992 |
| WO | WO-94/09209 | | | 4/1994 |
| WO | WO9409209 | | * | 4/1994 |
| WO | WO-96/35772 | A1 | | 11/1996 |
| WO | WO 96/39200 | | | 12/1996 |
| WO | WO-97/22684 | A1 | | 6/1997 |
| WO | WO-98/54285 | | | 12/1998 |
| WO | WO-99/50382 | | | 10/1999 |
| WO | WO-02/086043 | A1 | | 10/2002 |
| WO | WO-03/068901 | A1 | | 8/2003 |
| WO | WO-2006/138738 | A1 | | 12/2006 |

OTHER PUBLICATIONS

Written Opinion of ISA, PCT/IB2007/054854, dated Apr. 3, 2008 (6 pages).

Formo, M. W., et al., Bailey's Industrial Oil and Fat products, 4th Edition, vol. 1, pp. 558-560 (1979).

Ballman, D. K., et al., "Fungicides and germicides in the pulp and paper industry," *Paper Industry and Paper World*, (May 1943), 25, pp. 143-48.

Johnson, R. C., "Making mould a thing of the past," World pulp and paper technology (1996/1997), p. 59.

Ghosh, K. G., et al., "Development and Application of Fungistatic Wrappers in Food Preservation, Part II. Wrappers Made by Coating Process," *J. Fd. Sci & Technol.*, vol. 14, No. 6, Nov.-Dec. 1977, pp. 261-264.

Defence Standard: Wrapping, Mouldable, Waxed, Grease-Resisting, London, UK: HMSO for Ministry of Defence, Sep. 16, 1996, 16 pps. (supercedes DEF Spec 1237).

Schultz-Boedeker, Dieter F., "Properties, adaptability, and use possibilities of films." Fed. Rep. Ger., Seifen, Oele, Fette, Wachse (1973), (abstract).

Sauerbrunn, et al., "Moisture diffusion through bar soap wrappers by TGA," American Laboratory, Jan. 2004, pp. 22-25.

Whalley, G. R., "Soap Preservation," Soap/Cosmet./Chem. Spec, May 1990, 66 (5), 28-33.

"Jergens Clarifies Image with Printed Overwraps," Packag.Dig., (1004), vol. 31, No. 10, Sep. 1994, pp. 24, 26, 28.

"From soap to nuts, new biodegradable NatureFlex," Packag.World, (Oct. 2004), pp. 55-56, vol. 11, No. 10.

* cited by examiner

PACKAGING FOR HIGH MOISTURE BAR SOAP

CROSS REFERENCE TO RELATED APPLICATION

This application claims the benefit of U.S. Provisional Application No. 60/872,377 filed Dec. 1, 2006.

FIELD OF THE INVENTION

The present invention relates to packaging for high moisture bar soap compositions for cleansing skin.

BACKGROUND OF THE INVENTION

Bar soaps remain a popular product form for cleansing skin. Those skilled in the art use the term soap to designate the reaction product of a carboxylic acid with a base, typically a metal hydroxide or carbonate. The resulting salt has both a polar hydrophilic end and a non-polar lipophilic end which facilitates the removal of oils and other non-polar materials from the skin or other surface in the presence of water.

Bar soaps are customarily prepared either by framing/casting or by milling/plodding. The process of making bar soaps usually requires a drying step to remove the "gummy" texture and excessive pliability of the soap mass which exist typically at higher moisture levels. Finished bar soaps typically will thus have a relatively low level of moisture (i.e. water), usually in the range of from about 10% to about 14% by weight of the bar soap. However, developments have been made with respect to achieving bar soaps that contain higher moisture levels, e.g. at least about 15% water by weight of the bar soap. Bar soaps having higher levels of moisture can be desirable with respect to formulation and process efficiency. However, upon storage in conventional paperboard packaging, high moisture bar soaps tend to encounter of number of potential problems. These problems include moisture loss (via evaporation or absorption into the paperboard packaging material), mold growth on the paperboard packaging material, and the development of colored stains on the bar soap and packaging resulting from chemical reaction between the high moisture bar soap and the paperboard, especially recycled paperboard.

There thus remains a desire to develop a package for a high moisture bar soap to alleviate the problems of moisture loss, mold growth and dye transfer.

SUMMARY OF THE INVENTION

The present invention relates packaging for high moisture bar soap compositions to address a number of potential problems associated with high moisture bar soap compositions, such as minimizing moisture loss, inhibiting mold growth on paperboard material used in the packaging, and preventing the development of colored stains on the bar soap and packaging resulting from chemical reaction between the high moisture bar soap and the paperboard, especially recycled paperboard. The bar soap product of the present invention comprises: (a) a bar soap package comprising a laminate material and (b) a bar soap composition comprising at least about 15%, by weight of the bar soap composition, of water. The laminate material of the bar soap package comprises a paperboard material, a thermoplastic material disposed on at least one side of the paperboard material, and a fungicide. The paperboard material can be made of cellulosic fibers, either virgin pulp or recycled pulp. Recycled paperboard material is preferred. The thermoplastic material is preferably a biaxially oriented polypropylene material. The fungicide is preferably selected from the group consisting of carbendazim, chlorothalonil, p-tolyl diiodomethyl sulfone, thiabendazole, and mixtures thereof.

The present invention further relates to a method of inhibiting the growth of mold which can result from storage of a high moisture bar soap composition in a paperboard package. The method of inhibiting the growth of mold, especially the mold species *aspergillus sydowii* and/or *penicillium chrysogenum*, on a paperboard package containing a high moisture bar soap composition comprises treating the paperboard package with a fungicide comprising chlorothalonil and p-tolyl diiodomethyl sulfone, and then packaging the high moisture bar soap composition in the treated paperboard package.

DETAILED DESCRIPTION OF THE INVENTION

As used herein, the term "high moisture bar soap" refers to a bar soap composition comprising at least about 15%, preferably at least about 20%, by weight of the bar soap composition, of water.

Package

The bar soap package of the present invention comprises a laminate material comprising a paperboard material, a thermoplastic material, and a fungicide. The thermoplastic material is disposed, preferably laminated, on at least one side of the paperboard material. The thermoplastic material can be applied, preferably laminated, to a side of the paperboard material via a variety of methods, such as adhesive bonding, thermal bonding, and the like. The fungicide can be disposed on at least one side of the paperboard material and/or incorporated directly into the paperboard material during the process of manufacturing the paperboard material.

In one embodiment, the paperboard material is folded into a carton or box configuration to contain the high moisture bar soap composition. In this respect, the paperboard material will have an inner side which faces the interior of the carton or box, and an outer side that faces the external environment surrounding the carton or box. In one embodiment, the thermoplastic material is laminated onto the inner side of the paperboard material via an adhesive. If the carton or box includes any graphics on the outside of the carton or box, then such graphics are printed on the outer side of the paperboard material. Then, the fungicide is applied to the outer side of the paperboard material, on top of the printed graphics.

Suitable paperboard material includes materials made of fibers, such as cellulosic fibers. Such materials are commonly known in the art and preferably have a weight of from about 200 grams per square meter ("gsm") to about 500 gsm.

Suitable thermoplastic materials for use in the present invention include polypropylene (such as biaxially oriented polypropylene ("BOPP")), polyethylene, polyethylene terephthalate ("PET"), polyester, polyvinyl chloride ("PVC"), and combinations thereof. The thermoplastic materials used are preferably selected to retard the loss of moisture from the bar soap composition upon storage. The thermoplastic material is also preferably impermeable to water or water vapor, thereby retarding the absorption of water by the paperboard. The thermoplastic material is also preferably selected to prevent the development of colored stains on the bar soap and packaging resulting from chemical reaction between the high moisture bar soap and the paperboard, especially recycled paperboard. The thermoplastic material will typically have a thickness of from about 5 μm to about 100 μm, preferably from about 10 μm to about 50 μm, and more preferably from about 12 μm to about 25 μm. In one embodiment, the thermoplastic material is biaxially oriented polypropylene ("BOPP") having a thickness of 18 μm.

Suitable fungicides for use in the present invention include chlorothalonil, p-tolyl diiodomethyl sulfone, carbendazim, thiabendazole, and mixtures thereof. A preferred fungicide is carbendazim which is commercially available from Intace S.A. under the trade name INTACE B-350. Another preferred fungicide comprises a mixture of chlorothalonil and p-tolyl diiodomethyl sulfone, which is commercially available from Intace S.A. under the trade name INTACE B-6773. It is understood that many other suitable fungicides are known in the art and that the preceding list of fungicides are merely non-limiting examples. Fungicides are typically incorporated onto a side of the paperboard material, or directly into the paperboard material, at a level of from about 500 ppm to about 10,000 ppm, preferably from about 1000 ppm to about 5000 ppm, and more preferably from about 1500 ppm to about 3000 ppm.

Bar Soap Composition

The bar soap composition of the present invention comprises water, soap and other optional ingredients.

Water

The bar soap composition of the present invention comprises at least about 15%, more preferably at least about 20%, and more preferably at least about 25%, by weight of the composition, of water. The level of water can be still higher, e.g. 30%, 35%, or even 40%, but is typically not greater than about 60%, preferably not greater than about 55%, and more preferably not greater than about 50%, by weight of the bar composition.

It should be understood that an amount of water will be lost, i.e. evaporated, during the process of making the bar composition. Also, once the finished product is made, water can be further lost from the bar composition due to water evaporation, water being absorbed by surrounding packaging (e.g. a cardboard carton), and the like. Packaging the bar soap composition in a package of the present invention will reduce the amount of water lost due to evaporation upon storage or absorption into the package.

Soap

The bar compositions of the present invention will typically comprise from about 40% to about 84%, preferably from about 45% to about 75%, and more preferably from about 50% to about 65%, by weight of the composition, of soap. The term "soap" is used herein in its popular sense, i.e., the alkali metal or alkanol ammonium salts of alkane- or alkene monocarboxylic acids. Sodium, magnesium, potassium, calcium, mono-, di- and tri-ethanol ammonium cations, or combinations thereof, are suitable for purposes of the present invention. In general, sodium soaps are used in the compositions of this invention, but from about 1% to about 25% of the soap may be ammonium, potassium, magnesium, calcium or a mixture of these soaps. The soaps useful herein are the well known alkali metal salts of alkanoic or alkenoic acids having about 12 to 22 carbon atoms, preferably about 12 to about 18 carbon atoms. They may also be described as alkali metal carboxylates of alkyl or alkene hydrocarbons having about 12 to about 22 carbon atoms.

Soaps having the fatty acid distribution of coconut oil may provide the lower end of the broad molecular weight range. Those soaps having the fatty acid distribution of peanut or rapeseed oil, or their hydrogenated derivatives, may provide the upper end of the broad molecular weight range.

It can be preferred to use soaps having the fatty acid distribution of tallow, and vegetable oil. More preferably the vegetable oil is selected from the group consisting of palm oil, coconut oil, palm kernel oil, palm oil stearine, and hydrogenated rice bran oil, or mixtures thereof, since these are among the more readily available fats. Especially preferred are palm oil stearine, palm kernel oil, and/or coconut oil. The proportion of fatty acids having at least 12 carbon atoms in coconut oil soap is about 85%. This proportion will be greater when mixtures of coconut oil and fats such as tallow, palm oil, or non-tropical nut oils or fats are used, wherein the principle chain lengths are C16 and higher.

A preferred soap is sodium soap having a mixture of from about 50% to about 80%, more preferably from about 35% to about 40%, tallow; from 0% to about 60%, more preferably from 0% to about 50%, palm stearine; from 0% to about 40%, more preferably from 0% to about 35%, palm oil; and from about 10% to about 35%, more preferably from about 15% to about 30%, palm kernel oil or coconut oil.

The soaps may contain unsaturation in accordance with commercially acceptable standards. Excessive unsaturation is normally avoided.

Soaps may be made by the classic kettle boiling process or modern continuous soap manufacturing processes wherein natural fats and oils such as tallow or coconut oil or their equivalents are saponified with an alkali metal hydroxide using procedures well known to those skilled in the art. Alternatively, the soaps may be made by neutralizing fatty acids, such as lauric (C12), myristic (C14), palmitic (C16), or stearic (C18) acids with an alkali metal hydroxide or carbonate.

In one embodiment, the bar composition will comprise soap made by a continuous soap manufacturing process. The soap, which comprises approximately 30% water, is then processed into soap noodles via a vacuum flash drying process. The soap noodles preferably comprise about about 85% anhydrous soap (50% tallow/30% palm oil stearine/20% palm kernel oil (or 20% coconut oil)), about 0.2% free citric acid, about 0.2% sodium citrate, about 0.05% tetrasodium DPTA, about 0.05% tetrasodium HEDP, about 0.6% sodium chloride, about 1% glycerin, and from about 12% to about 18% water, the balance being unsaponifiables. These percentage amounts are by weight of the soap noodles. The soap noodles are then utilized in a milling process to make the finished bar composition as described below.

Inorganic Salts

Inorganic salts can be optionally utilized in the present bar compositions to help in maintaining the relatively high water content of the present compositions. The inorganic salts help to bind the water in the bar composition thereby preventing water loss by evaporation or other means. The present bar compositions comprise from about 1% to about 15%, preferably from about 2% to about 12%, and more preferably from about 2.5% to about 10.5%, by weight of the composition, of inorganic salt. Suitable inorganic salts include magnesium nitrate, trimagnesium phosphate, calcium chloride, sodium carbonate, sodium aluminum sulfate, disodium phosphate, sodium polymetaphosphate, sodium magnesium succinate, sodium tripolyphosphate, aluminum sulfate, aluminum chloride, aluminum chlorohydrate, aluminum-zirconium trichlorohydrate, aluminum-zirconium trichlorohydrate glycine complex, zinc sulfate, ammonium chloride, ammonium phosphate, calcium acetate, calcium nitrate, calcium phosphate, calcium sulfate, ferric sulfate, magnesium chloride, magnesium sulfate, and the like. Preferred inorganic salts include sodium tripolyphosphate, magnesium salts (such as magnesium sulfate), and/or tetrasodium pyrophosphate. Magnesium salts, when used as an ingredient in the present bar compositions comprising soap, tend to be converted to magnesium soap in the finished product. Sodium tripolyphosphate, magnesium salts (and as a result magnesium soap), and/or tetrasodium pyrophosphate are preferred in the present compositions Sodium tripolyphosphate is also preferred as it can tend to promote the generation of lather as the bar composition is used by a consumer for cleansing skin.

Carbohydrate Structurants

Carbohyrate structurants can optionally, but preferably, be included as ingredients in the present bar compositions. Carbohydrate structurants tend to assist in maintaining the relatively high level of water in the present compositions. Suitable carbohydrate structurants as ingredients in the present compositions include raw starch (corn, rice, potato, wheat, and the like), pregelatinzed starch, carboxymethyl cellulose, stabylene, carbopol, carregeenan, xanthan gum, polyethylene glycol, polyethylene oxide, and the like. Preferred carbohydrate structurants include raw starch and/or pregelatinized starch.

A preferred carbohydrate structurant for incorporating in a bar composition is starch. The starch can be either raw starch or it can be pregelatinized starch. Alternatively, raw starch can be used and modified during the process of making the bar composition such that the starch becomes gelatinized, either partially or fully gelatinized. Pregelatinized starch is starch that has been gelatinized before added as an ingredient in the present bar compositions. Gelatinized starch, either partially or fully gelatinized starch, can be preferred for providing enhanced skin feel benefits, such as providing a soft and smooth skin feel. A preferred pregelatinized starch for use as an ingredient in the present compositions is PREGEL-A M 0300 commercially available from Tianjin Tingfung Starch Development Co., Ltd. of Tianjin, China.

The level of carbohydrate structurant in the present compositions is typically from about 1% to about 20%, preferably from about 2% to about 17%, and more preferably from about 4% to about 15%, by weight of the composition.

The bar soap compositions of the present invention can further comprise additional optional ingredients such as humectants (e.g. glycerin or sorbitol), free fatty acids, synthetic surfactants, cationic polymers, brighteners, silica, and the like. Such optional ingredients are described in more detail in co-pending U.S. application Ser. No. 11/453,767, filed Jun. 15, 2006, and U.S. Provisional Application Ser. No. 60/811,545, filed Jun. 6, 2006.

Other optional ingredients in the present bar compositions include: perfumes; sequestering agents, such as tetrasodium ethylenediaminetetraacetate (EDTA), EHDP or mixtures thereof typically in an amount of 0.01 to 1%, preferably 0.01 to 0.05%, by weight of the composition; and coloring agents, opacifiers and pearlizers such as titanium dioxide; all of which are useful in enhancing the appearance or cosmetic properties of the product.

The pH of a 1% solution of the bar composition of the present invention dissolved in water is typically from about 7 to about 12, preferably from about 8 to about 11, and more preferably from about 9 to about 10.

The appearance of the bar composition according to the present invention can be transparent, translucent, or opaque. In one embodiment, the bar composition is opaque.

Suitable high moisture bar soap compositions that can benefit from being packaged in the bar soap package of the present invention include those bar soap compositions described in detail in co-pending U.S. application Ser. No. 11/453,767, filed Jun. 15, 2006, and U.S. Provisional Application Ser. No. 60/811,545, filed Jun. 6, 2006.

The cleansing bar compositions of the present invention can be used by consumers to cleanse skin during bathing or washing.

Method of Inhibiting Growth of Mold

The present invention further relates to a method of inhibiting the growth of mold, especially certain species of mold such as *aspergillus sydowii* and/or *penicillium chrysogenum*, that can grow on a paperboard package containing a high moisture bar soap composition. It has been found that the mold species *aspergillus sydowii* and/or *penicillium chrysogenum* can be especially problematic with respect to growing on paperboard packages containing high moisture bar soaps. Such mold species are typically resistant to commonly-used fungicides on paperboard packaging materials, such as carbendazim.

It has further been found that treating the paperboard packaging materials with a fungicide that comprises a mixture of chlorothalonil and p-tolyl diiodomethyl sulfone can effectively inhibit the growth of mold on the paperboard packaging, especially certain species of mold such as *aspergillus sydowii* and/or *penicillium chrysogenum*. Such a fungicide material is commercially available from Intace S.A. under the tradename INTACE B-6773.

In one embodiment, the method comprises treating a paperboard package with a fungicide comprising chlorothalonil and p-tolyl diiodomethyl sulfone and using the package to contain a bar soap composition comprising at least about 15%, by weight of the bar soap composition, of water.

EXAMPLES

The following are non-limiting examples of the cleansing bar compositions that are contained in the bar soap packaging of the present invention. Amounts of each ingredient are approximate weight percentages by weight of the bar composition.

| Ingredient | Example 1 | Example 2 | Example 3 | Example 4 |
|---|---|---|---|---|
| Soap Noodle[a] | 58.00% | 58.00% | 58.00% | 58.00% |
| Raw Corn Starch | 12.09% | 8.76% | 6.54% | 3.20% |
| Magnesium Sulfate | — | 3.00% | 5.00% | 8.00% |
| Dye Solution | 0.50% | 0.02% | 0.02% | 0.02% |
| Perfume | 0.90% | 0.90% | 0.90% | 0.90% |
| Sodium Tripolyphosphate | 2.50% | 2.50% | 2.50% | 2.50% |
| Titanium Dioxide | 0.50% | 0.50% | 0.50% | 0.50% |
| Palm Kernel Fatty Acid | 0.75% | 0.75% | 0.75% | 0.75% |
| Approximate Water Lost During Processing | (1%) | (1%) | (1%) | (1%) |
| Approximate Water Content in Finished Product | 20-25% | 20-25% | 20-25% | 20-25% |

| Ingredient | Example 5 | Example 6 | Example 7 | Example 8 |
|---|---|---|---|---|
| Soap Noodle[a] | 58.00% | 58.00% | 54.00% | 54.00% |
| Raw Corn Starch | 3.54% | 4.50% | 9.25% | 9.25% |
| Magnesium Sulfate | 8.00% | — | — | — |
| Tetrasodium Pyrophosphate | — | 8.00% | 8.00% | 8.00% |
| Dye Solution | 0.50% | 0.50% | 0.50% | 0.50% |
| Perfume | 0.90% | 0.90% | 0.90% | 0.90% |
| Sodium Tripolyphosphate | 2.50% | 2.50% | 2.50% | 2.50% |
| Titanium Dioxide | 0.50% | 0.50% | 0.50% | 0.50% |
| Palm Kernel Fatty Acid | 0.75% | 0.75% | 1.50% | 0.75% |
| Sodium Laureth 3 Sulfate | — | — | — | 0.75% |
| Approximate Water Lost During Processing | (1%) | (1%) | (1%) | (1%) |

-continued

| Ingredient | Example 9 | Example 10 | Example 11 | Example 12 |
|---|---|---|---|---|
| Approximate Water Content in Finished Product | 20-25% | 20-25% | 20-25% | 20-25% |

| Ingredient | Example 9 | Example 10 | Example 11 | Example 12 |
|---|---|---|---|---|
| Soap Noodle[a] | 58.00% | 58.00% | 54.00% | 54.00% |
| Glycerin | — | — | 3.00% | 3.00% |
| Raw Corn Starch | — | 12.50% | 17.00% | 12.50% |
| Tetrasodium Pyrophosphate | 8.00% | — | — | 3.00% |
| Brightener | 0.02% | 0.02% | — | — |
| Perfume | 0.90% | 1.20% | 1.40% | 1.40% |
| Sodium Tripolyphosphate | 2.50% | 2.50% | 2.50% | — |
| Titanium Dioxide | 0.50% | 0.50% | 0.50% | 0.50% |
| Palm Kernel Fatty Acid | 0.75% | 0.75% | — | — |
| Sodium Lauryl Sulfate | — | — | 0.10% | 0.10% |
| Pregelatinized Starch[b] | 4.50% | — | — | — |
| Trichlorocarban | — | — | 0.60% | 0.60% |
| Dye Solution | 0.50% | 0.50% | 0.50% | 0.50% |
| Approximate Water Lost During Processing | (1%) | (1%) | (1%) | (1%) |
| Approximate Water Content in Finished Product | 20-25% | 20-25% | 20-25% | 20-25% |

[a]The Soap Noodle utilized in these examples has the following approximate composition: about 85% Anhydrous Soap (50% Tallow/30% Palm Oil Stearine/20% Palm Kernel Oil (or 20% Coconut Oil)), about 0.2% Free Citric Acid, about 0.2% Sodium Citrate, about 0.05% Tetrasodium DPTA, about 0.05% Tetrasodium HEDP, about 0.6% Sodium Chloride, about 1% Glycerin, and from about 12% to about 18% Water, the balance being unsaponifiables. These percentage amounts are by weight of the Soap Noodle.
[b]Pregelatinized starch is available as PREGEL-A M 0300 from Tianjin Tingfung Starch Development Co., Ltd. of Tianjin, China.

In these examples, the Soap Noodles are made via a conventional process involving a crutching step and a vacuum drying step. The Soap Noodles are then added to an amalgamator. The ingredients of perfume, brightener, and titanium dioxide are then added to the amalgamator and mixed for about 10 to 15 seconds. The ingredients such as water, inorganic salts (such as sodium tripolyphosphate, tetrasodium pyrophosphate, and/or magnesium sulfate), free fatty acid (such as palm kernel fatty acid), carbohydrate structurant (such as raw starch or pregelatinized starch), dye solution, and trichlorocarban are then added to the amalgamator and then mixed for about 30 to 45 seconds. This soap mixture is then processed through conventional milling, plodding, and stamping steps to yield the finished bar soap compositions. The finished bar soap compositions are then contained in a bar soap package of the present invention.

The dimensions and values disclosed herein are not to be understood as being strictly limited to the exact numerical values recited. Instead, unless otherwise specified, each such dimension or value is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of inhibiting the growth of mold on a paperboard package containing a bar soap composition comprising at least about 15%, by weight of said bar soap composition, of water, said method comprising:
- (a) treating said paperboard package with a fungicide comprising chlorothalonil and p-tolyl diiodomethyl sulfone; and
- (b) packaging said bar soap composition in said treated paperboard package.

2. The method of claim 1, wherein said paperboard package comprises a thermoplastic material disposed on at least one side of said paperboard package.

3. The method of claim 2, wherein said thermoplastic material is selected from the group consisting of polypropylene, polyethylene, polyethylene terephthalate, polyester, polyvinyl chloride, and mixtures thereof.

4. The method of claim 3, wherein said thermoplastic material is biaxially oriented polypropylene.

5. The method of claim 1, wherein said method inhibits the growth of mold species selected from the group consisting of *aspergillus sydowii, penicillium chrysogenum*, and mixtures thereof.

6. The method of claim 1, wherein said fungicide is disposed on at least one side of said paperboard material, incorporated directly in said paperboard material, or a combination thereof.

7. The method of claim 1, wherein said paperboard package comprises cellulosic fibers.

8. The method of claim 7, wherein the cellulosic fibers are at least partially recycled.

9. The method of claim 2, wherein said paperboard material has an outer side and an inner side, said thermoplastic material being disposed on said inner side of said paperboard material.

10. The method of claim 9, wherein said fungicide is disposed on said outer side of said paperboard material.

11. The method of claim 2, wherein said thermoplastic material is impermeable to water, water vapor, or a combination thereof.

12. The method of claim 2, wherein said thermoplastic material has a thickness of about 5μm to about 100μm.

13. The method of claim 2, wherein said thermoplastic material has a thickness of about 10μm to about 50μm.

14. The method of claim 2, wherein said thermoplastic material has a thickness of about 12μm to about 25μm.

* * * * *